United States Patent [19]
Morita

[11] Patent Number: 5,628,765
[45] Date of Patent: May 13, 1997

[54] LANCET ASSEMBLY

[75] Inventor: Susumu Morita, Nishinomiya, Japan

[73] Assignee: APLS Co., Ltd., Okayama-ken, Japan

[21] Appl. No.: 463,696

[22] Filed: Jun. 5, 1995

[30] Foreign Application Priority Data

Nov. 29, 1994 [JP] Japan .................................. 6-294793

[51] Int. Cl.$^6$ ..................................................... A61B 17/34
[52] U.S. Cl. ........................... 606/182; 604/136; 606/181
[58] Field of Search .................................. 606/181, 182, 606/183, 167; 604/136

[56] References Cited

U.S. PATENT DOCUMENTS

| | | |
|---|---|---|
| Re. 32,922 | 5/1989 | Levin et al. . |
| 3,030,959 | 4/1962 | Grünert . |
| 3,358,689 | 12/1967 | Higgins . |
| 4,375,815 | 3/1983 | Burns . |
| 4,379,456 | 4/1983 | Cornell et al. . |
| 4,388,925 | 6/1983 | Burns . |
| 4,414,975 | 11/1983 | Ryder et al. . |
| 4,416,279 | 11/1983 | Lindner et al. . |
| 4,442,836 | 4/1984 | Meinecke et al. . |
| 4,449,529 | 5/1984 | Burns et al. . |
| 4,452,243 | 6/1984 | Leopoldi et al. . |
| 4,462,405 | 7/1984 | Ehrlich . |
| 4,469,110 | 9/1984 | Slama . |
| 4,503,856 | 3/1985 | Cornell et al. . |
| 4,514,609 | 4/1985 | Fricke et al. . |
| 4,517,978 | 5/1985 | Levin et al. . |
| 4,527,561 | 7/1985 | Burns . |
| 4,535,769 | 8/1985 | Burns . |
| 4,539,988 | 9/1985 | Shirley et al. . |
| 4,545,376 | 10/1985 | Beiter . |
| 4,553,541 | 11/1985 | Burns . |
| 4,577,630 | 3/1986 | Nitzsche et al. . |
| 4,580,564 | 4/1986 | Andersen . |
| 4,580,565 | 4/1986 | Cornell et al. . |
| 4,610,667 | 9/1986 | Pedicano et al. . |
| 4,616,649 | 10/1986 | Burns . |
| 4,624,253 | 11/1986 | Burns . |
| 4,648,408 | 3/1987 | Hutcheson et al. . |
| 4,653,513 | 3/1987 | Dombrowski . |
| 4,658,821 | 4/1987 | Chiodo et al. . |
| 4,676,244 | 6/1987 | Enstrom . |
| 4,677,979 | 7/1987 | Burns . |
| 4,712,548 | 12/1987 | Enstrom . |
| 4,715,374 | 12/1987 | Maggio . |
| 4,735,203 | 4/1988 | Ryder et al. . |
| 4,738,261 | 4/1988 | Enstrom . |
| 4,794,926 | 1/1989 | Munsch et al. . |
| 4,817,603 | 4/1989 | Turner et al. . |
| 4,844,095 | 7/1989 | Chiodo et al. . |
| 4,856,515 | 8/1989 | Turner et al. . |

(List continued on next page.)

FOREIGN PATENT DOCUMENTS

| | | |
|---|---|---|
| MR 0933 1992 | 10/1992 | Denmark . |
| 0633004A1 | 1/1995 | European Pat. Off. . |
| 92 05 278 | 6/1992 | Germany . |

OTHER PUBLICATIONS

Lagana, "Guide to Finger–Pricking Equipment," *Diabetese Self–Management* (R.A. Rapaport Publishing, Inc.), 7, 6–11 (Jul./Aug. 1990).

Modulohm A/S Catalog (1992).

*Primary Examiner*—Michael Powell Buiz
*Assistant Examiner*—Mark S. Leonardo
*Attorney, Agent, or Firm*—Leydig, Voit & Mayer, Ltd.

[57] ABSTRACT

There is provided a lancet assembly having a holder and a lancet structure which is incorporated with the holder, the lancet structure containing a lancet member having a pricking member and an ejector which ejects the lancet member, wherein an exposed portion of the pricking member is covered with a resin. In a preferred embodiment, a lancet body and a covered pricking member have portions mating each other so that the lancet body and the covered pricking member tightly engage with each other. In another preferred embodiment, at least one notch is provided to the covered pricking member. In a further embodiment, the covered pricking member contains two pairs of stops on its outside.

12 Claims, 9 Drawing Sheets

U.S. PATENT DOCUMENTS

| | | |
|---|---|---|
| 4,858,607 | 8/1989 | Jordan et al. . |
| 4,869,249 | 9/1989 | Crossman et al. . |
| 4,889,117 | 12/1989 | Stevens . |
| 4,892,097 | 1/1990 | Ranalletta et al. . |
| 4,924,879 | 5/1990 | O'Brien . |
| 4,976,724 | 12/1990 | Nieto et al. . |
| 4,990,154 | 2/1991 | Brown et al. . |
| 4,994,068 | 2/1991 | Hufnagle . |
| 4,995,402 | 2/1991 | Smith et al. . |
| 5,026,388 | 6/1991 | Ingalz . |
| 5,047,044 | 9/1991 | Smith et al. . |
| 5,074,872 | 12/1991 | Brown et al. . |
| 5,100,427 | 3/1992 | Crossman et al. . |
| 5,105,823 | 4/1992 | Blum . |
| 5,133,730 | 7/1992 | Biro et al. . |
| 5,147,375 | 9/1992 | Sullivan et al. . |
| 5,207,699 | 5/1993 | Coe . |
| 5,314,442 | 5/1994 | Morita . |
| 5,397,334 | 3/1995 | Schenk et al. ............ 606/182 |
| 5,439,473 | 8/1995 | Jorgensen . |
| 5,487,748 | 1/1996 | Marshall et al. ............ 606/182 |

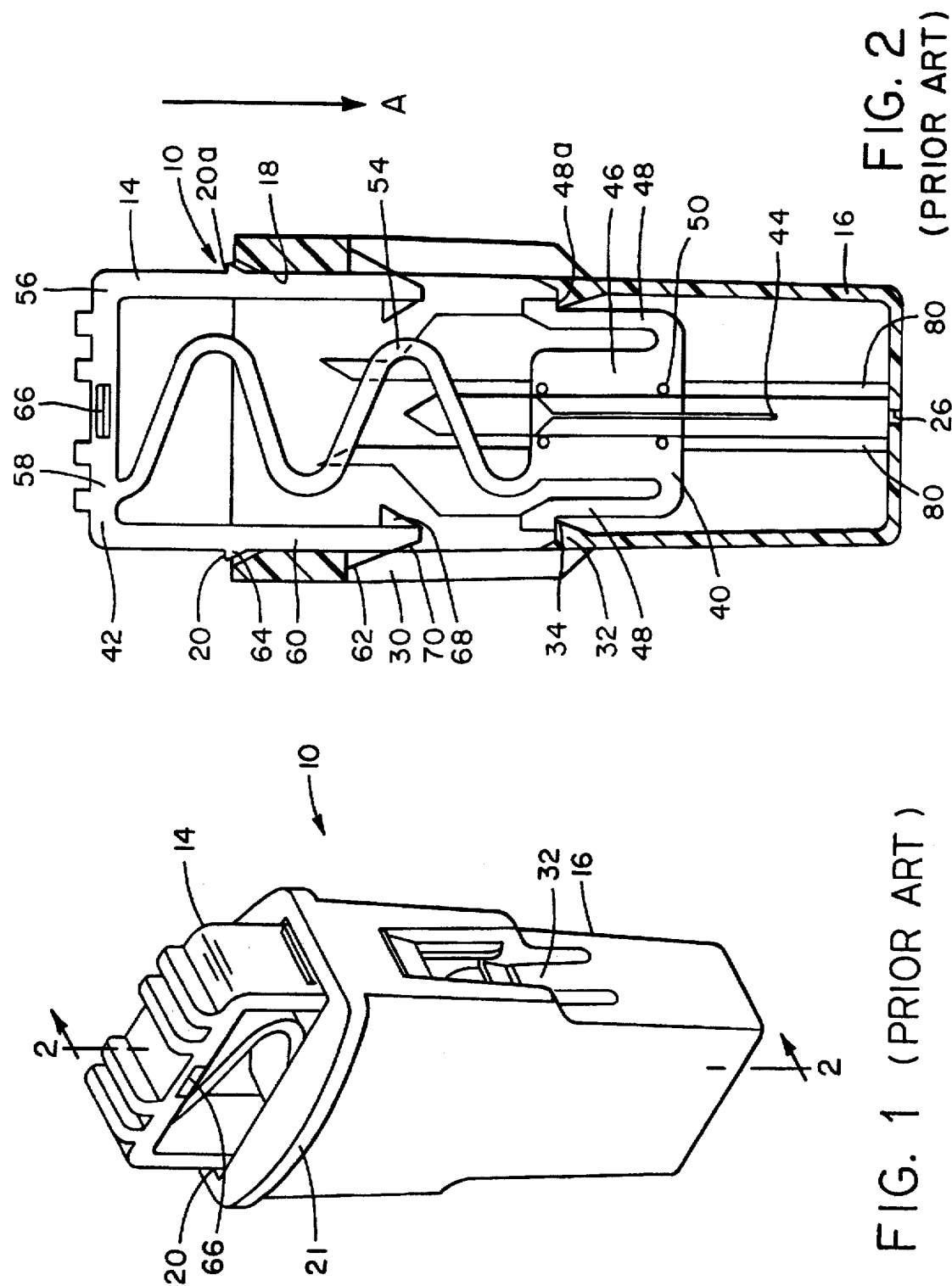

LANCET ASSEMBLY

FIELD OF INVENTION

The present invention relates generally to a lancet assembly or a pricking device such as a finger pricking device which wounds skin to permit the collection of a small amount of blood. More specifically, the invention is directed to such an assembly which ensures sterility of the lancet before its use and which is also disposable and adapted for only a single-use.

BACKGROUND OF THE INVENTION

Various lancet assemblies or finger-pricking devices are commercially available to hospitals, clinics, doctors' offices, and the like, as well as to individual consumers. Such devices include a sharp-pointed member or a sharp-edged member, sometimes called a pricking member (such as a blade-like member or a needle-like member) that is used to make a quick puncture or incision of the patient's skin in order to provide a small outflow of blood. Various tests may be employed using only small amounts of blood so that blood flowing from such a wound or puncture is normally sufficient for these tests.

Such lancet assemblies are typically sterilized beforehand, and maintained in a sterile condition before use to ensure that the lancet is not contaminated by its surrounding environment. In addition, in order to prevent the lancet from wounding a user of the assembly or any other object around the user upon contact of the pricking member therewith during handing the assembly, the pricking member generally should not be physically exposed.

After using of the assembly, extra care must be taken by the user to avoid being punctured by a used lancet assembly. The risks in handling used lancets are greatly increased due to present day concerns regarding communicable diseases transmitted through body fluids such as blood (e.g. blood born diseases). Accordingly, the lancet assembly must be carefully handled until it can be properly disposed. Advances have been made in recent years to increase safety in handling such used devices. For example, pricking devices are currently available which include the features of automatic ejection and retraction of the blade edge tip, or a single shot firing mechanism.

One such lancet assembly, for example, is shown in Danish Design Patent No. MR 0933 (granted on Oct. 1, 1992). The Danish Design Patent lancet assembly is a self-contained device that includes a lancet structure, which includes a unitary ejector (projector or injector) and lancet element, used in combination with a holder (or a protective sheath or sleeve). The lancet structure is contained in the holder after use.

The Danish Design Patent lancet assembly is commercially available from Modulohm A/S (Denmark) under a trade name of Vitrex, of which structure is schematically shown in FIGS. 1 to 7, wherein FIG. 1 shows a lancet assembly 10 before its use wherein a lancet structure 14 is incorporated into a holder 16;

FIG. 2 schematically shows a partial cross-sectional front view of the lancet assembly taken along line 2—2 in FIG. 1;

FIG. 3 schematically shows a cross-sectional front view which is similar to the view shown in FIG. 2 wherein the lancet structure 14 is disposed inside of the holder 16;

FIG. 4 schematically shows a cross-sectional front view which is similar to the view shown in FIG. 2 wherein the lancet structure 14 is being ejected for its use;

FIG. 5 schematically shows a cross-sectional front view which is similar to the view shown in FIG. 2 showing the lancet structure 14 and holder 16 after use;

FIG. 6 schematically shows an exploded perspective view of the lancet structure 14 of FIG. 1 before a blade 44 has been mounted; and FIG. 7 schematically shows a perspective view of the lancet structure 14 after the blade 44 has been inserted.

The shown lancet assembly 10 essentially comprises a unitary lancet structure 14 and a holder 16. It is preferable that the lancet structure 14 of the lancet assembly 10, excluding the pricking member 44 (for example a blade member), be made of a polymer, such as a polyacetal (POM) resin, a polybutylene terephalate resin or a polyester copolymer resin for the member 14, and the holder 16 be made of an acrylonitrile-butadiene-styrene (ABS) resin, a polycarbonate resin or a polyester copolymer resin, each being injection molded as a unitary structure. During use, the members 14 and 16 move between the relative positions shown in FIGS. 2, 3, 4 and 5 sequentially.

The holder 16 includes a cavity 18 extending along an ejecting direction of the lancet structure 14 which cavity cooperates with an opening 20 for receiving the unitary lancet structure 14. Adjacent the opening 20 are outwardly extending flanges 21, as shown in FIG. 1, which are used to hold the holder 16 between the fingers of the user during operation of the lancet assembly 10. The cavity 18 includes guidance channels 80 on and along opposite sides of the inner wall of the cavity 18, which channels cooperate with mating protrusions 50 (such as pins) provided on a lancet body 46 of the lancet structure 14 so as to smoothly control movement of the lancet body 46 within the cavity 18. The opposite end of the holder 16 relative to the opening 20 is provided with an aperture 26 through which, during use of the assembly 10, a tip portion of the pricking member 44 protrudes and then retracts.

The holder 16 further includes channels or openings 30 along opposite sides, which open into the cavity 18 (and thus the channels pass through the walls of the holder). For further controlling movement of the unitary lancet structure 14 within the holder 16, arms 32 of the holder 16 disposed within the openings 30 include engaging protrusions (or extensions) 34, which extend into the cavity 18. The significance of these members will become clear upon a more detailed explanation of the unitary lancet structure 14.

The unitary lancet structure 14 comprises a lancet member 40 and an ejector 42. The lancet member 40 includes a pricking member (such as a blade or a needle) 44 and a lancet body 46 having cantilevered arms 48. To guide movement of the lancet member 40 through the holder 16, pins 50 are provided on the remaining opposite sides of the lancet body 46. As the lancet structure 14 is positioned within the holder 16 and actuated, the pins 50 cooperate with the guidance channels 80 provided on the inner walls of the cavity 18 to control the periscoping movement of the lancet member 40 along the channels 80 within the holder 16. The pricking element 44 of the lancet member 40, which is secured to and protrudes from one side of the lancet body 46, is formed from stainless steel or the like and includes a sharp point for piercing the patient's skin.

The ejector 42 includes a compressible spring member 54 and a U-shaped actuator 56. The U-shaped actuator 56 includes a base portion 58, to which the compressible spring member 54 is coupled, and upstanding actuator arms 60. The opposite end of the spring member 54 is attached to the lancet body 46. The lancet structure 14 is sized such that it may be disposed and move within the opening 20 and cavity 18 of the holder 16 in the positions shown in FIGS. 2 to 5.

To retain the lancet structure 14 in place within the opening 20 and the cavity 18 of the holder 16 prior to actuation of the lancet assembly 10, as shown in FIG. 2, outwardly extending lips (protrusions) 62 and 64 are provided along the outer surfaces of the actuator arms 60. In this position, the lips 62 are disposed within the channels 30 such that each of the lips 62 extends outward and seats against the upper edge of each channel 30. As a result, the lancet structure 14 cannot be pulled out of the holder 16 even though it is drawn along a direction opposite to the arrow A.

In the position shown in FIG. 2, the lips 64 are disposed adjacent the opening 20 of the holder 16. It may be noted that the outer surfaces of the lips 64 are tapered upwardly from the opening 20 so that the U-shaped actuator 56 easily slides into the holder 16 with cooperation of a tapered portion 20a (so called guiding portion) of the wall edge forming the opening 20 when the actuator 56 is depressed into the holder 16.

The lips 64 further function to lock the lancet structure 14 in position within the holder 16 after actuation (or use) of the assembly 10. Namely, as seen from FIG. 5 which shows a position after use, the lips 64 are disposed within the respective channels 30 such that they may abut against the upper edge of each channel 30 as a stop so as to prevent the members 14 and 16 from separating from each other (substantially the same position previously occupied by the lips 62 in the unactuated position of FIG. 3).

The actuator arms 60 function as an actuator for releasing (or ejecting) the lancet member 40 to permit the blade end 44 to protrude from the aperture 26, as will be apparent from the explanation set forth below. The end of each actuator arm 60 is provided with an inwardly tapered lip 68 along the inner surface of the arm 60, and an outwardly tapered lip 62 having an outside surface 70.

The operation of the lancet assembly 10 will be described with reference to FIGS. 2–5. Prior to actuation of the assembly, the members 14 and 16 of the assembly 10 are disposed in the relative positions shown in FIG. 2. To use the assembly, the user takes the holder 16 between his fingers and places the end of the holder 16 containing the aperture 26 against the skin of the patient. The user then uses his thumb to depress the U-shaped actuator 56 into the holder 16 along a direction of the arrow A, as shown in FIG. 2. As the actuator 56 is depressed, the engaging protrusions 34 of the holder 16 contact extensions 48a on the cantilevered arms 48 of the lancet member 40 so that the arms 48 cannot further proceed and the lancet member 40 is held in this initial position. As a result of the lancet member 40 being held in this position, the protrusions 34 compress and energize the spring member 54 as the user continues to depress the actuator 56.

As the user further continues to depress the actuator 56, the ends of the actuator arms 60 approach and contact or almost contact the engaging protrusions 34 and then separate (or release) the extensions 48a of the cantilevered arms 48 of the lancet member 40 from the engaging protrusions 34 of the holder 16, as shown in FIG. 3. As the engaging protrusions 34 and the arms 48 disengage from the abutting position thereof, the compressed spring member 54 is no longer restrained, and releases the accumulated energy to eject the lancet member 40 toward the aperture 26, as shown in FIG. 4. The compressed spring 54 extends such that the lancet member 40 moves to a position as shown in phantom in FIG. 4, so that the pricking member 44 protrudes from the aperture 26 to pierce the skin. After extension, the spring member 54 returns to its free-state position, as shown in solid lines in FIG. 5.

In the prior art lancet assembly using the blade as described above, the pricking member 44 is not shielded (or covered) and it is exposed. Namely, the blade edge 44 of the lancet structure 14 incorporated into the holder 16 is not covered at all and it is exposed within the holder 16. Therefore, each individual lancet assembly in the position as shown in FIG. 1 must be packed as a unit in a blister package or a resin made container, the whole of which has to then be sterilized. This type of packaging and sterilization is relatively expensive (the cost for the sterilization is proportional to a volume including the package).

As shown in FIG. 6, the lancet structure 14 is assembled by inserting the exposed blade 44 in the direction of the arrow. FIG. 7 shows the position of the blade 44 and lancet structure 14 after the insertion. In order to assemble the lancet assembly 10, the lancet structure 14 is inserted into the holder 16 while the blade 44 is exposed as in FIG. 7. Therefore, a step is required in which the blade 44 is exposed during handling (for example, a step in which the blade 44 is inserted to form the lancet structure 14 or a step in which the lancet structure 14 having the inserted blade 44 is inserted into the holder 16). In any such a step, since the blade 44 is exposed, its edge (or tip) is likely to contact another object so that the edge will very likely be damaged or otherwise injure the handling person. Further, the blade 44 is very likely to be contaminated with microorganisms such as a bacteria.

SUMMARY OF THE INVENTION

It is an object of the present invention to overcome the problems just described above, and other problems which will be understood from the following description of the present invention and preferred embodiments thereof.

According to a first aspect of the present invention, there is provided a lancet assembly as described above characterized in that a pricking member is covered (or shielded) with a resin. Namely, the lancet assembly according to the present invention comprises a holder and a lancet structure. The lancet structure comprises a lancet member having a pricking member and an ejector which ejects the lancet member. The assembly is characterized in that an exposed portion of the pricking member is shielded with a resin shield.

Further, according to a second aspect of the present invention, the lancet member comprises a pricking member, which is covered with a resin and a lancet body. The lancet body and the shielded pricking member mate such that the lancet body and the covered pricking member tightly engage with each other.

In addition, according to a third aspect of the present invention, the covering resin is provided with at least one notch at a predetermined position at which the resin is to be broken so that the covering resin is easily broken when it is pulled along an ejection direction of the pricking member, whereby the pricking member is exposed with ease. This embodiment of the present invention is particularly effective in lancets in which the pricking member is in the form of a blade.

Further, according to a fourth aspect of the present invention, the covered pricking member comprises two sets of stops along its outside surface. The stops are positioned such that an aperture of a holder through which the pricking member passes is located between the two sets of the stops.

In any of the above lancet assemblies according to the present invention, the holder used therein may have a structure which is substantially the same as that of the holder (or sleeve) of the Danish Design Patent which has been described in the "BACKGROUND OF THE INVENTION" section of this specification. Similarly, the lancet structure of the present invention, for example an ejector mechanism, may have the same structure of the Danish Design Patent except the covered pricking member.

These features and other features of the present invention as well as effects provided by those features will be understood by the following description of some preferred and illustrative embodiments of the present invention and with reference to accompanying drawings.

It should be noted that although the present invention will be described with reference to the preferred embodiments, especially an embodiment in which the pricking member is in the form of the blade, the present invention is not limited to such an embodiment and applicable to any other pricking member, such as a needle, provided that no substantially adverse problem occurs.

BRIEF DESCRIPTION OF THE DRAWINGS

FIG. 1 schematically shows a perspective view of a lancet assembly 10 of the prior art before use;

FIG. 2 schematically shows a partial cross-sectional view of the lancet assembly taken along line 2—2 in FIG. 1;

DETAILED DESCRIPTION OF THE INVENTION

Figure 8:
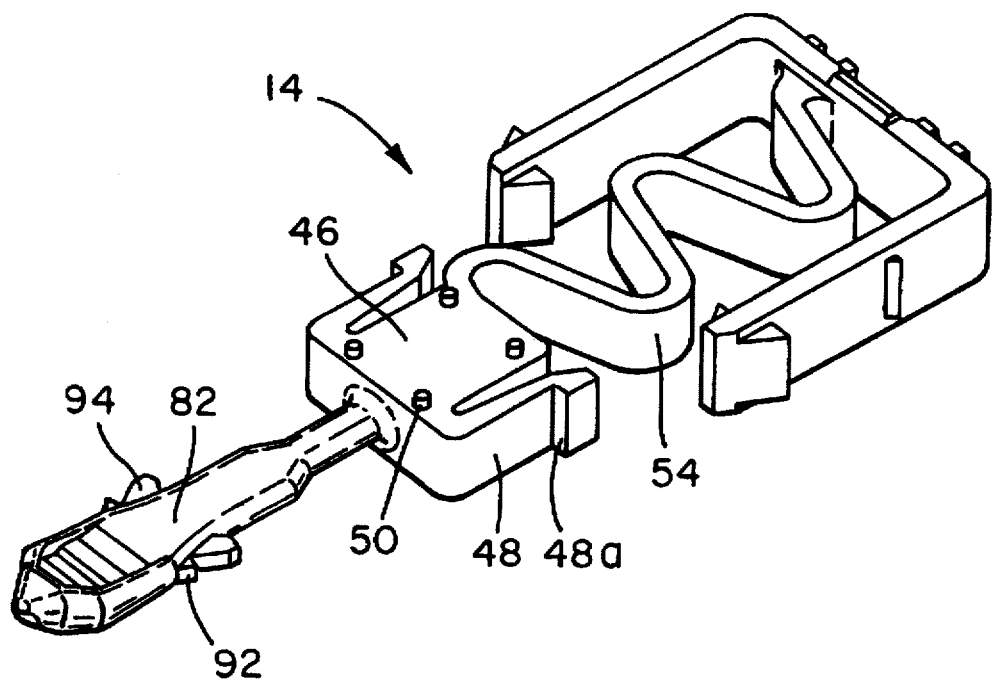
FIG. 8 schematically shows a perspective view of a lancet structure of a lancet assembly constructed in accordance with teachings of the present invention.
Figure 9:
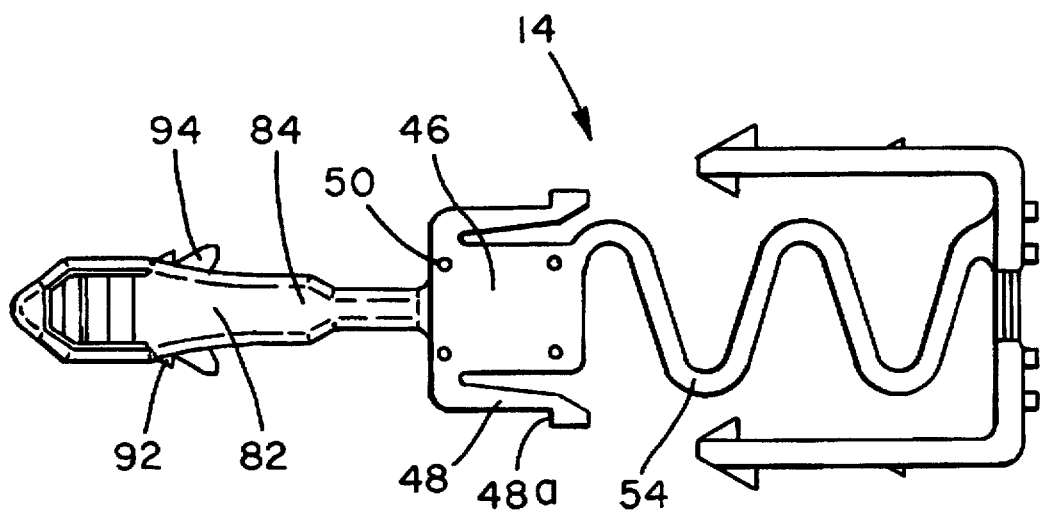
FIG. 9 schematically shows a plane view of the lancet structure shown in FIG. 8.

A lancet structure 14 according to the present invention is shown in the perspective view of FIG. 8 and the plane view of FIG. 9. In these drawings, the pricking member 44 (for example, a blade such as that shown exposed in the prior art lancet assembly as described above in connection with FIGS. 1–7) is now covered or shielded with a resin portion 82, and thus is not visible in the drawings. Other than this covering or shield, the lancet structure 14 may be substantially the same as the lancet structure of the Danish Design Patent which has been described in the above; the lancet structure 14 functions and effects provided by said other features are substantially the same as those provided by such a prior art lancet structure.

Formation of such a resin cover or shield 82 may be carried out in various manners and any known suitable manner may be used. For example, a lancet structure 14 can be molded while the blade 44 is held. Alternatively, a cover part 82 having a cavity in the form of a sheath into which the pricking member 44 can be inserted and a lancet body 46 containing the blade 44 with its exposed edge portion may be separately formed beforehand. The exposed edge portion of the blade 44 may then be inserted into the cavity of the part 82 and the parts 46 and 82 secured together by any suitable means such as ultrasonic welding or an adhesive.

The resin cover 82 is preferably so formed that its tip portion protrudes from the aperture 26 of the holder 16 when the lancet structure 14 is incorporated into the holder 16 prior to use, whereby the protruding tip portion of the resin cover can be easily pulled using fingers. The resin cover 82 preferably has a portion along which tensile strength is weakened to such an extent that the resin cover may be removed to expose the pricking member 44 by merely pulling the tip portion of the resin cover 82, as described above. To provide such weakened tensile strength, the resin cover 82 has a thinned section at a certain predetermined point so that the resin cover is likely to be broken at that point.

When the pricking member 44 is covered with the resin cover 82, the sharp tip (or edge) portion of the pricking member 44 does not contact any other object upon incorporation of the lancet structure 14 into the holder 16. As a result, the tip portion of the blade will not damage other objects and/or the tip not be damaged by other objects.

In addition, since the pricking member 44 is not exposed, only the structure 82 including the pricking member 44 requires sterilization so that individual lancet assemblies need not be packed into sterile packages, greatly reducing the costs of packing, as well as sterilizing costs.

Figure 10:
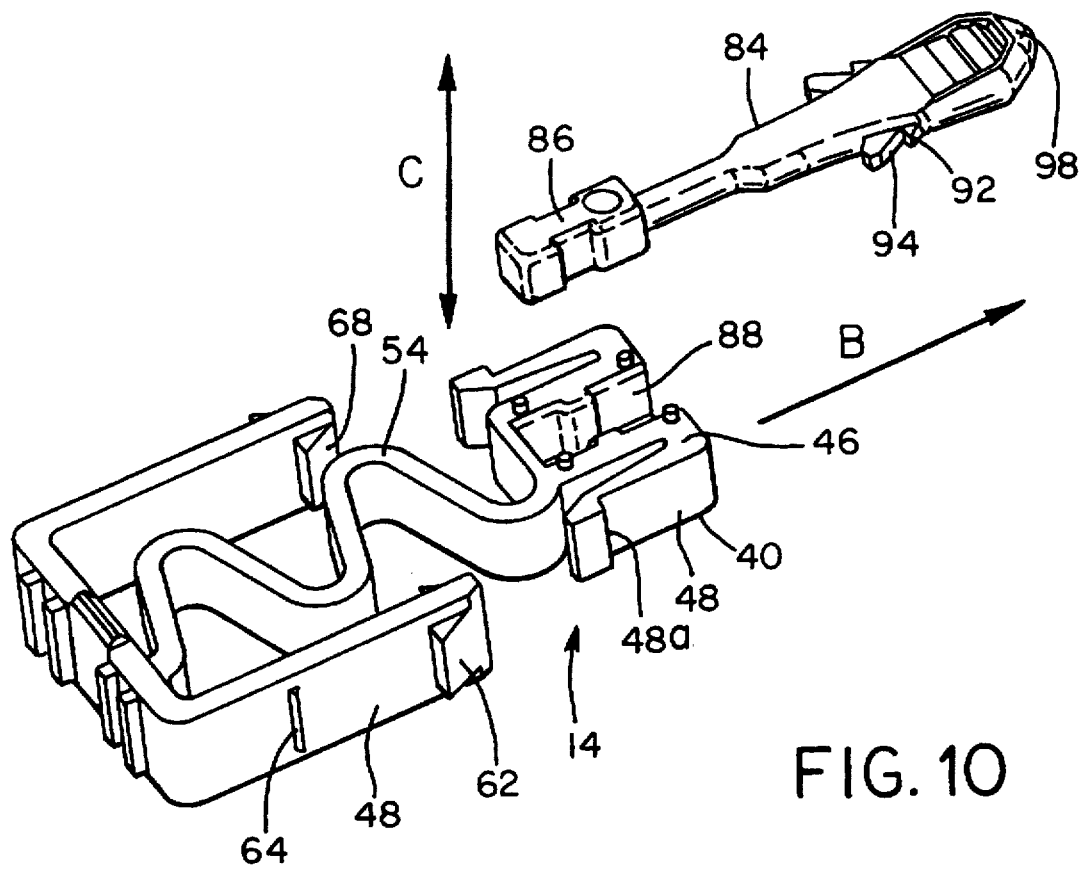
FIG. 10 schematically shows an exploded perspective view of a lancet structure of a second embodiment constructed in accordance with teachings of the present invention.

FIG. 10 schematically shows an exploded perspective view of an alternate embodiment of the lancet structure 14 of a lancet assembly according to another aspect of the present invention.

In the lancet structure 14, a lancet member 40 comprises a lancet body 46 and a covered pricking member 84 (the covered pricking member 84 refers to the assembly including the pricking member 44 and the resin cover 82). The members 46, 84 are molded separately from one another and are provided with engaging elements which couple the members 46, 84 together. The covered pricking member 84 includes an engaging element 86 at an end thereof (opposite to an ejecting direction) which has an overall convex shape. The lancet body 46 includes an engaging element 88 which comprises an overall concave shape at its end opposite the end connected to the spring member 54.

As may be seen from FIG. 10, the lancet body 46 comprises the concave engaging element 88, and the covered pricking member 84 comprises the convex engaging element 86 which mates with the concave engaging element 88 along a direction of the arrow C (for example with press fitting). As seen from the drawing, the convex and concave shapes of the engaging elements 86, 88, respectively, couple the covered pricking member 84 and the lancet body 46 together such that they can withstand a tensile force along a direction of a lancet body ejection (arrow B). In this regard, the lancet body 46 and the covered pricking member 84 may not be disconnected by merely applying a force with one's fingers. However, these members 46, 84 may be separated from one another upon application of a sufficient, relative vertical force applied in the direction of arrow C.

The engaging elements 86 and 88 may be in any complementary forms provided that the members including the elements withstand the force of the arrow B and they are combined substantially along the direction of arrow C to achieve the engaging relationship. Generally, the engaging elements may be formed by combining various sets of complementary concave and convex portions.

In order to form a covered pricking member 84, the resin cover may be formed on the pricking member 44 to form a covered pricking member 84 by, for example, an injection molding process. The cavities of metal molds may be arranged to provide an optimal configuration of the covered pricking member 84 when the lancet body 46 is combined or mated therewith.

For example, a portion of the covered pricking member 84, preferably a base portion thereof, may be so arranged that its configuration is suitable for the connection to the engaging element 88 of the lancet body 46 with any suitable manner such as press fitting, snap fitting, ultrasonic welding or caulking.

It is also preferred that the configuration of the resin covered pricking member 84 is suitable for mechanical manipulation or processing. For example, a partially wide configuration is advantageous in that the covered pricking member 84 may be picked up using a mechanical chuck or an air chuck for the incorporation of the covered pricking member 84 into the lancet body 84.

This is in contrast to prior art devices which are produced by incorporating a metal (stainless steel in most cases) blade itself as a single member into a lancet body. In as much as a stainless steel blade is small and light (typically 2.5 mm width×12 mm length×0.16 mm thickness and 0.28 to 0.30 g per blade), it is more likely that a typical "picking up" means, such as the air chuck or mechanical chuck, would fail to pick up a single blade (as in the prior art) than the inventive covered pricking member 84 when incorporating the blade into the lancet body. In addition, it is more difficult to transport a blade for incorporation into the lancet body because the blade is light and magnetized, and, as a result, the blade will not fall stably upon when released.

In addition, the only possible manners by which the pricking member 44 could be connected to the lancet body 46 in the prior art device have been to use an adhesive or to partially heat-deform an objective member (i.e. the lancet body). These manners are not suitable for mass production.

In contrast, according to the present invention, the pricking member 44 is covered with resin to produce a separate covered pricking member 84. A portion of the member 84 is so (widely) configured that it is suitable for picking up, whereby its configuration becomes suitable for the incorporation onto the lancet body as described above. Thus, the covered pricking member 84 results in a more optimal size, a more optimal weight, cancellation of a magnetic force effect and a more suitable shape for picking up, transferring, releasing, incorporating the covered pricking member into and connecting it to the lancet body in comparison with the use of a single blade itself. As a result, it is possible to continuously incorporate the member 84 onto the lancet body 46 accurately and stably using an automatic machine.

Further, it is possible to use a manner to connect the resin covered pricking member 84 to the lancet body 46 that is suitable for continuous mass production, as, for example, by press fitting, snap fitting, ultrasonic welding or caulking. These manners are superior to the case in which the blade alone is incorporated with respect to connection accuracy and connection strength.

With respect to the lancet structure according to the present invention, covering the pricking member with the resin and forming into a necessary shape as the covered pricking member can be continuously and automatically carried out in a clean room by endless insert hoop molding and metal molds fabricated for the formation of the necessary shape as the lancet structure. The possibility of the mass production and the reduced overall cost are very important factors for devices which are used for medical treatments in high volumes.

In accomplishing another aspect of the present invention, a notch may be provided in the resin cover 82 at a predetermined breaking position in order that only the cover 82 (substantially in the form of the sheath), which covers and protects the pricking member 44 of the unitary lancet structure 14, can be broken and removed just before the use of the assembly.

The term "notch" as used herein is intended to mean a weakened portion (for example, a cut-into portion or a cut-away portion) of the resin cover which permits the resin cover to be broken at a predetermined position upon the application of a force along a direction of the arrow B in FIG. 10. A notch may be formed by partially thinning a portion of the resin cover (namely, by providing a neck portion to the cover resin). More specifically, a U-shaped or V-shaped cross sectional portion is formed at an intended break position of the resin cover (so that such a portion has a reduced thickness). In the preferred embodiments, the metal molds are so arranged that the notch is simultaneously formed when the cover resin is integrally molded, or a sharp blade is used to cut a notch into the resin cover after molding. It is of course possible to form the notch and to then further cut into the notch.

Figure 11:
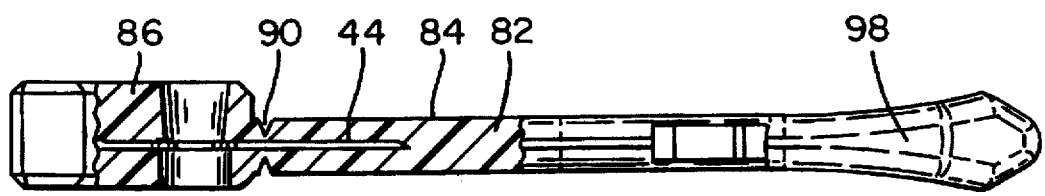
FIG. 11 schematically shows a side view of a covered pricking member.
Figure 12:
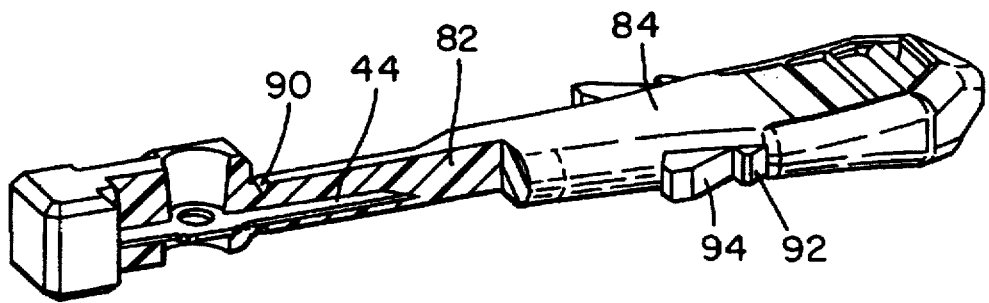
FIG. 12 shows a partially cut-away perspective view of the pricking member of FIG. 11.

An embodiment in which the resin cover comprises notches is shown in FIGS. 11 and 12, which schematically show a side view and a perspective view, respectively, of a resin covered pricking member 84 which has been partially cut away to show the position of the pricking member 44. As seen from FIGS. 11 and 12, the pricking member 44 is rotated by 90° around an axis along the ejection direction as compared to the position of the pricking member 44 shown in the prior art lancet assembly of FIG. 2. The orientation of the pricking member 44 shown in FIG. 11 is preferable in order to provide a compact construction of lancet assembly, but other orientations of the pricking member may be possible. For example, the orientation as shown in FIG. 2 may be employed.

As clearly seen from the drawings, the notches 90 are formed at the predetermined break position of the resin cover 82. The predetermined break position may be any position, provided that breaking the resin cover 82 exposes the tip portion of the pricking member 44. At least one notch is formed into at least one of the opposing main (front and back) surfaces of the cover, which notch is usually perpendicular to the ejection direction of the lancet structure. In a preferred embodiment, the notches 90 are formed on the both surfaces of the resin symmetrically to the pricking member 44 as shown is the drawings. Usually, it is suitable that the notches 90 are formed near the lancet body 46.

The notch 90 is preferably formed using a tool having a sharp edge after the resin cover has been molded around the pricking member. A depth of the notch 90 is controlled so that an end (or a bottom) of the notch 90 does not reach the pricking member 44. Thus, the sterile condition of the shielded blade 44 is assured prior to use of the assembly.

A practical thickness of the resin which covers the pricking member 44 is in the range of about 1.4 to 2.0 mm, and it is thus sufficient that the depth of the notch is in the range of about 0.3 to 0.4 mm. It has been confirmed experimentally that the provision of the notch, in principle, makes the break strength of the cover sharply decrease regardless of the depth of the notch when resin is used for the cover 82.

Although the notch may be formed by the metal molds upon the molding as described above, the effect of the provision of the notch is more pronounced when the notch is formed with a tool after molding.

The effect of the notch described above is preferably achieved when the pricking member 44 is in the form of the blade, namely when the pricking member is thin and its cross section is substantially rectangular.

In a prior art lancet assembly using the pricking member in the form of the needle, a resin made cover cap protecting the needle can be removed from a body by twisting it just before use so as to break the resin. Such a prior art needle type lancet is so configured that a "neck portion" is provided at an intended break position to easily break the resin by twisting the cap.

Conversely, since the cross section of the blade in a blade type lancet assembly is not circular but rectangular (a typical cross section is 2.5 mm width×0.16 mm thickness), it is impossible to twist the cover resin around the blade. Accordingly, it is impossible to twist the assembly in order to break the resin. Therefore, in a blade type lancet assembly, it is essential that the user be able to easily break the resin cover at a predetermined break position and pull off the sheath-like resin cover in a manner other than twisting the resin cover.

In the case of the needle type lancet assembly, since a force to pull apart the cap is in the range of about 0.3 to 0.5 kg after twisting, the predetermined standard force for separating the resin cover 82 from the blade 44 in a blade type lancet assembly would optimally be at similar force levels.

In order to achieve such a predetermined force for breaking the resin cover, the inventor produced the blades from a stainless steel plate and used metal molds to injection mold various kinds of the blade structures which were covered with a polyethylene resin (i.e. covered pricking member). The blade structures were then tested. The inventor found that resin covers wherein the notch was formed at the predetermined break point (or intended position) in a region spaced from the engaging element toward the tip of the pricking member using a proper tool (a razor blade of which edge was blunted was used in the tests) achieved the predetermined break force.

In the tests, four types of the resin covered pricking members were used. Two types had two notches, one each provided on an upper side and a bottom side of the pricking member, which were molded at predetermined break positions using the metal molds; the thicknesses of the neck portion, including the blade thickness, were 1.2 mm and 1.6 mm, respectively. Two types had two notches, one each provided on an upper side and a bottom side of the pricking member, which were cut into the molded resin at the predetermined break positions using a razor blade (i.e. notches were not molded into the resin cover); the depths of the notches were 0.3 mm and 0.5 mm, respectively. The resin used was a linear low density polyethylene. The thickness of a portion of a resin covered pricking member without the notch (including the thickness of the blade) was 2.2 mm as a whole. A tensile tester was used to measure the force required to break the resin cover.

TEST (1): Each resin cover having molded notches was broken at the notches. The average force required to break 10 pieces was about 1.8 kg for 1.2 mm neck thickness, and about 2.0 kg for 1.6 mm neck thickness.

TEST (2): Each resin cover having notches cut in the molded part using a razor blade was broken at the notches. The average force required to break 10 pieces was in the range of about 0.3 to 0.4 kg and there was no clear dependency on the depth of the notch.

TEST (3): When a shallow (or short) rift (0.1 to 0.2 mm in length) was further formed at the notch which had been formed on the molding, a force required for the break was reduced to 0.25 to 0.3 kg.

TEST (4): The tensile tests were carried out without the formation of the notches. In the tests, the resin was stretched or broken at a position which was not indented.

From the above results, it has been found that the formation of the notch(es) at the predetermined position is effective, that the notch formed with the razor blade is more advantageous than that formed during the molding (namely, a sharper notch is more effective), and especially that the additional notch formation after the molding with notch formation is more effective.

Thus, it has been confirmed that, by using a tool to form a notch at a predetermined position of the blade structure in a premolded resin cover, where the notch has a depth which does not adversely affect the sterile condition of the blade member, the blade can be tightly sealed and the sterile condition of the blade can be kept until its use, and the blade resin cover can be pulled away with a relatively small force.

The material for the resin cover is not limited to a polyethylene (PE) resin. A polypropylene (PP) resin, an ABS resin, a polyacetal (POM) resin or a polyamide (PA) resin or copolymers of these polymers may be used.

The depth of the notch may be selected depending on the material used, especially its strength.

According to another aspect of the present invention, the resin cover shielding the pricking member may comprise two pairs of protrusions as stops. These stops are useful in preventing the notch(es), which is provided on the resin cover, from being broken.

Figure 13:
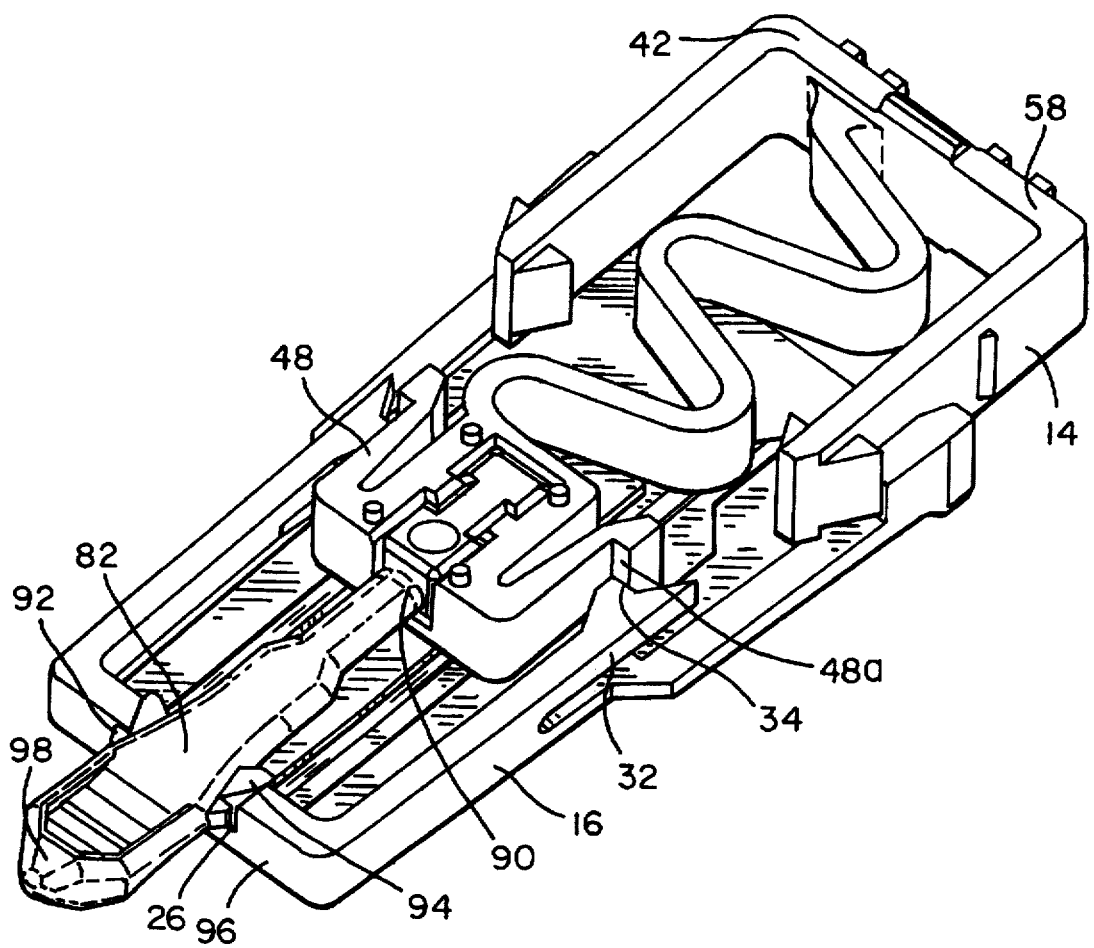
FIG. 13 schematically shows a perspective view of a lancet assembly according to the present invention in which an upper half portion of a holder is cut away so as to easily understand a position inside the holder.
Figure 14:
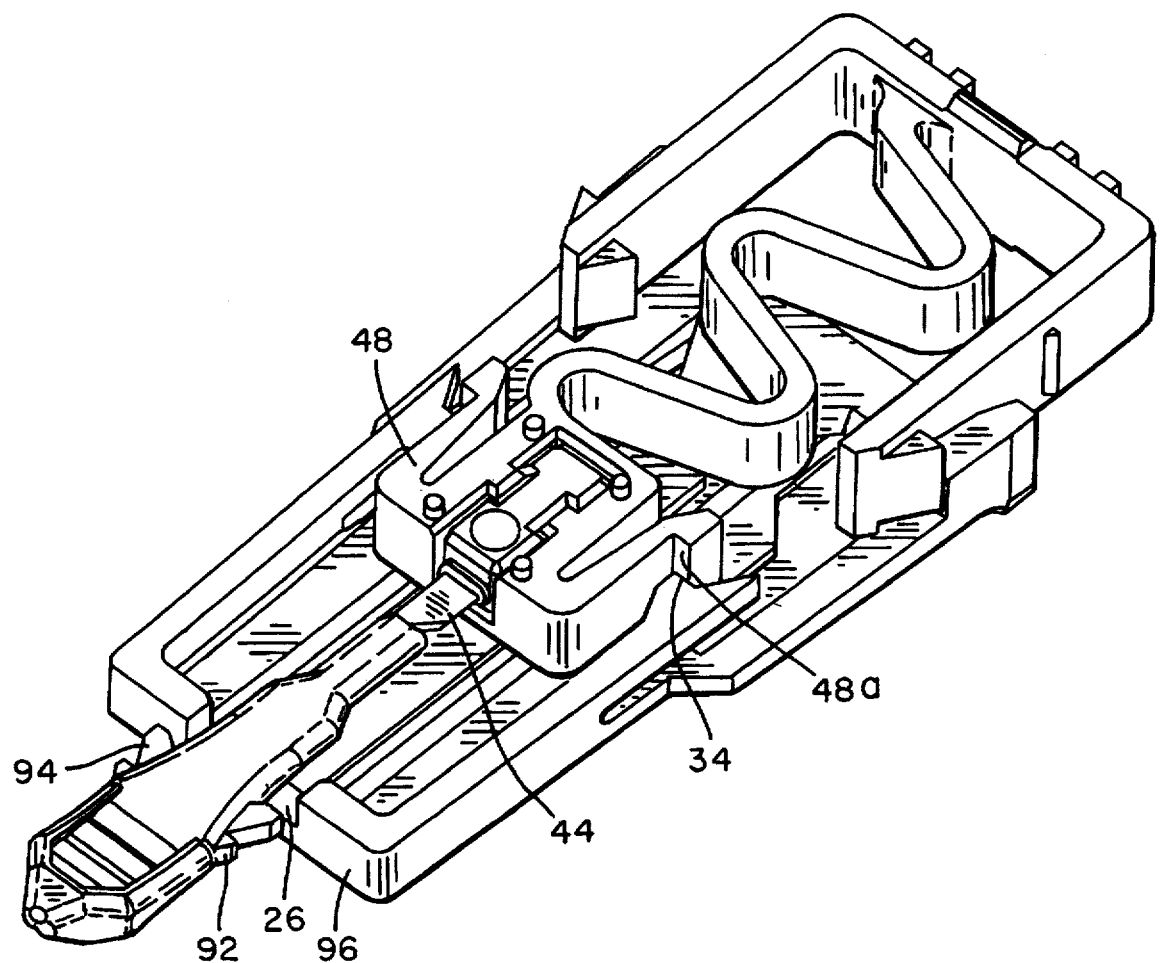
FIG. 14 shows a perspective view similar to that shown in FIG. 13, wherein the stops are in different positions and the pricking member is partially exposed.

That is, the resin cover 82 may be pulled away from the resin covered pricking member 84 along the notch. Thus, in order that the sheath-like resin cover is not easily removed from the lancet body until it is pulled away for the use of the lancet assembly, the pairs of the stops (the first pair of the stops 92 and the second pair of stops 94) are provided on proper positions outside the resin covered pricking member 84 as shown in FIGS. 13 and 14. These two pairs of the stops also function to hold the sheath member in place and keep such a position during final incorporation of the assembly.

Further, these two pairs of the stops also function as an indicator which shows whether or not the sheath-like resin cover 82 is in place (namely, whether the resin cover 82 is properly connected to the lancet body 46) and thus whether or not the blade remains sterile.

These protrusions are preferably in a double pair formation (i.e. the first row stops and the second row stops), and by positioning the end surface 96 of the holder 16 between the first and the second rows of the protrusions, the stops 92, 94 prevent the sheath-like resin cover from unduly being depressed into or pulled out of the holder 16. (As a result, the sheath-like resin cover 82 is prevented from being unduly broken at the notch portion.) The width of the stops (i.e. the distance between the outermost ends of the respective pairs of protrusions) in each of the first row and the second rows is larger than the width of the aperture 26 provided through the end surface 96 of the holder 16. For example, when the width of the aperture is 4.8 mm, the width of the first stops is in the range of about 4.9 to 5.0 mm, and the width of the second stops is in the range of about 5.4 mm. Since the resin is resilient, the first stops 92 can pass through the aperture 26 when the lancet structure 14 is incorporated into the holder 16, and the second stops 94 can also pass through the aperture 26, as shown in FIG. 14, when the resin cover 82 is removed just before the use of the lancet assembly. The protrusions are so shaped that their widths decrease along the ejection direction of the pricking member 44 so that the pricking member 44 (not shown in FIGS. 13 and 14) cannot be reversibly depressed into the holder 16 once the protrusions has been outside.

The provision of the protrusions results in the following three effects:

First, the protrusions prevent accidental breakage of the sheath-like resin cover such as may result from various stresses (such as a force to pull out the covered resin of the holder, a force to twist the covered resin or a composed force thereof) continuously applied to the covered pricking member during transportation of the lancet assembly. In this way, the sterile condition of the blade is stably and readily maintained.

As described in the Examples set forth below, one hundred sets of lancet assemblies were produced according to the present invention, and 25 pieces per batch were placed in a paper box, which was then placed in a pan of an ultrasonic bowl feeder. The bowl feeder was continuously operated for one week and none of the resin covers 82 were broken or removed from the lancet structure, and all the pieces were normal.

Secondly, the protrusions visually indicate whether or not the sterile and normal condition of the pricking member 44 has been maintained prior to use.

When only the first stops 92 are exposed outside from the end surface 96 and the second stops 94 are inside the holder 16 so that they cannot be seen from the outside (as shown in FIG. 13), the resin cover is in place (namely, the assembly is intact) so that the resin cover has not been broken at the notch portion 90, whereby the pricking member 44 is sterile (thus, since the lancet assembly is intact and safely in the sterile condition, it can be used for the usual application).

When the first stops 92 are not exposed outside the holder 16, such a position means an improper incorporation of the lancet assembly and such an assembly should not be used.

Further, when the first stops 92 and the second stops 94 are both exposed outside of the holder 16, such a position indicates that the resin cover 82 may be broken at the notch portion 90, which indicates that such a lancet assembly should not be used. This position of the stops is shown in FIG. 14 in which the resin sheath is broken and the pricking member 44 is exposed.

Therefore, the user should only use the lancet assembly if the first stops 92 alone are exposed. Also during inspection of production of the lancet assemblies in the factory, a defective assembly can be rejected by means of the first stops as the indicator.

In a needle type lancet assembly, the user can determine whether a cap and a lancet body are integrated or separated due to break by the level of resistance to twisting and by visual observation. Such visual observation is impossible for the blade type lancet assembly since the structure containing the blade is contained within the holder in most cases. As a result, the presence of the indicator as described above is very important in that it visually indicates whether or not the blade is safely and normally protected.

With respect to the blade type assembly, when the force required to cause the second stops to pass through the holder aperture is larger than the force required to break the resin cover at the notch portion, desirable results are obtained. As a result, the depth of the notch (a force required for the break) is selected first, then the size of the holder aperture, and then the size of the second stops are made larger stepwise to determine an optimal size (i.e. an optimal resistive force on passing through the aperture) of the second stops.

Thirdly, the second stops prevent the sheath-like resin cover from being twisted in error.

As a general example for the stops and the aperture, when, for example, the height of the holder inside (namely, the length of the inside of the holder perpendicular to the ejection direction of the lancet structure and also perpendicular to the width direction of the stops) is 4.3 mm and the stops width is 5.4 mm, the covered pricking member 84 cannot be twisted (or turned) in the holder 16 since the stopper width is larger than the height. This means that even though the user in error tries to twist the covered pricking member 84 so as to remove it, the member 84 is never twisted in the holder 16. This prevents serious defects such as bending and damaging of the pricking member 44 due to unduly forced twisting of the member 84.

Figure 15:
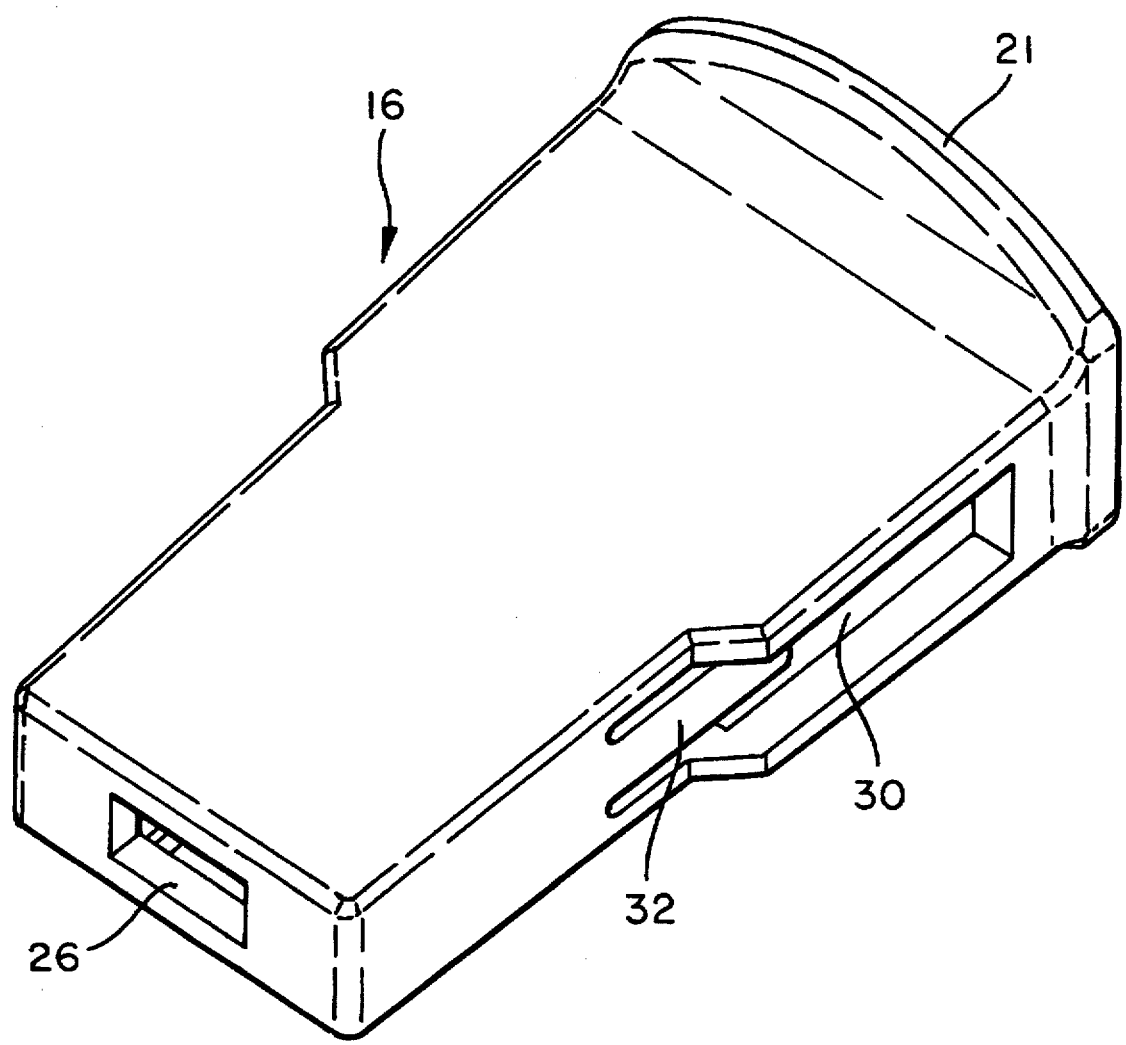
FIG. 15 shows a perspective view of a holder which may be used for the lancet assembly according to the present invention.

In an embodiment described above, the holder 16 used for the lancet structure is substantially the same as the holder 16 shown in FIG. 1, which holder is shown alone in FIG. 15.

EXAMPLES

Figure 4:
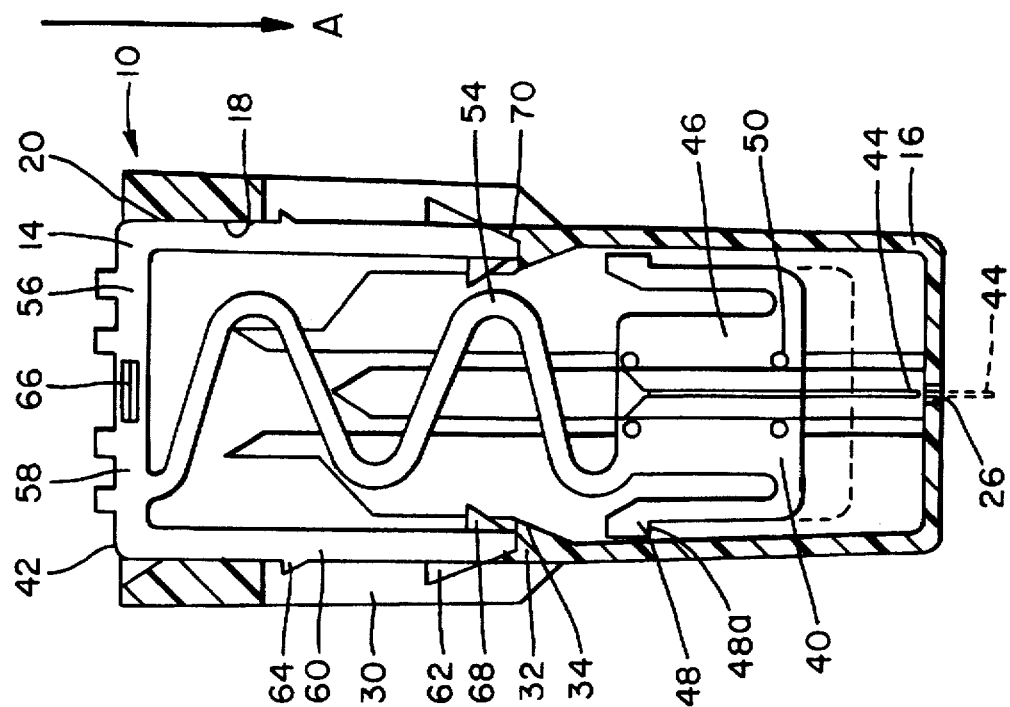
FIG. 4 is a cross-sectional schematic front view similar to the view shown in FIG. 2 showing in broken lines the lancet structure 14 being ejected from the holder 16 for use.
Figure 3:
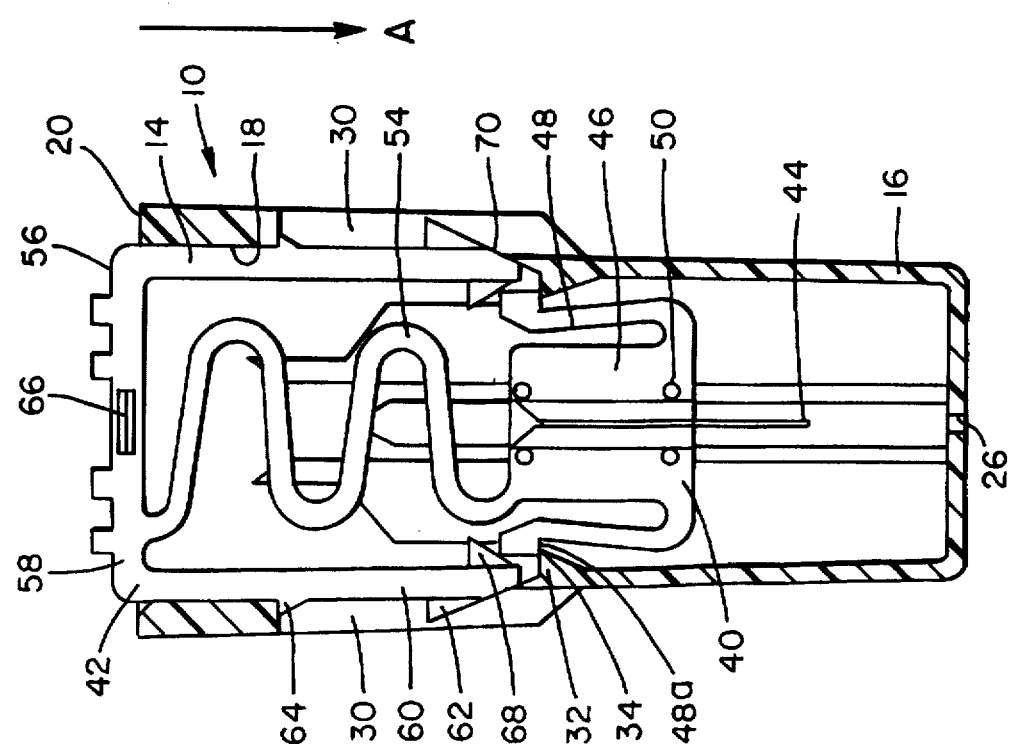
FIG. 3 is a cross-sectional schematic front view similar to the view shown in FIG. 2 wherein the lancet structure 14 is disposed inside of the holder 16.
Figure 5:
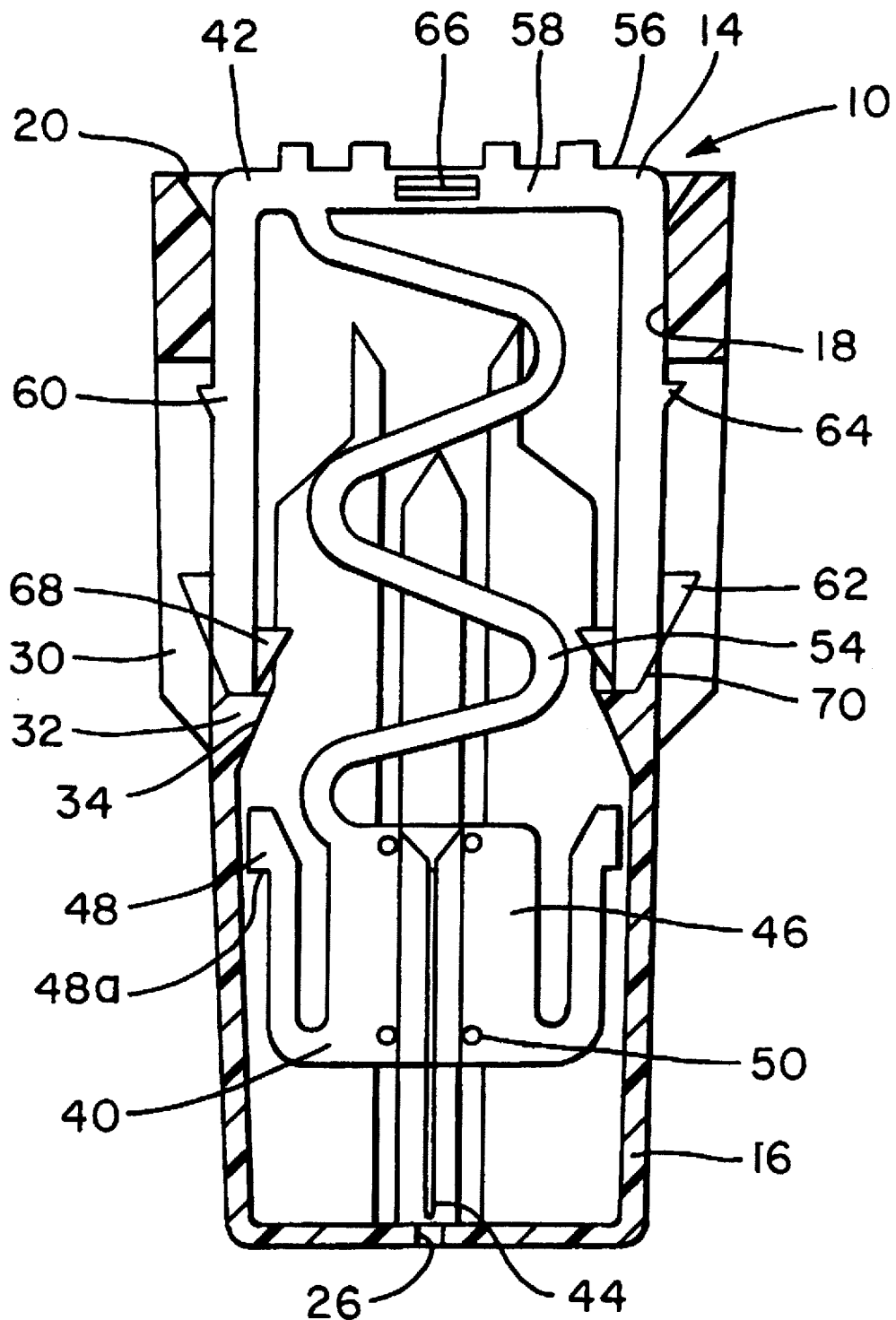
FIG. 5 is a cross-sectional schematic front view similar to the view shown in FIG. 2 showing the lancet structure 14 and holder 16 after use.
Figure 6:
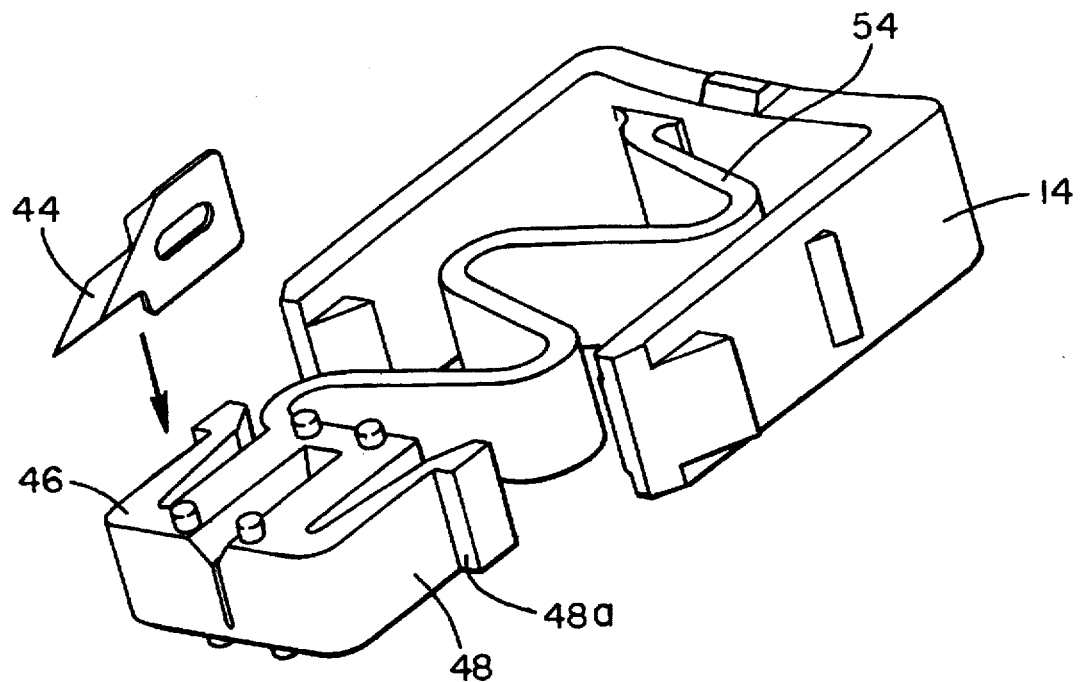
FIG. 6 schematically shows an exploded perspective view of the lancet structure 14 of FIG. 1 before a blade 44 has been mounted.
Figure 7:
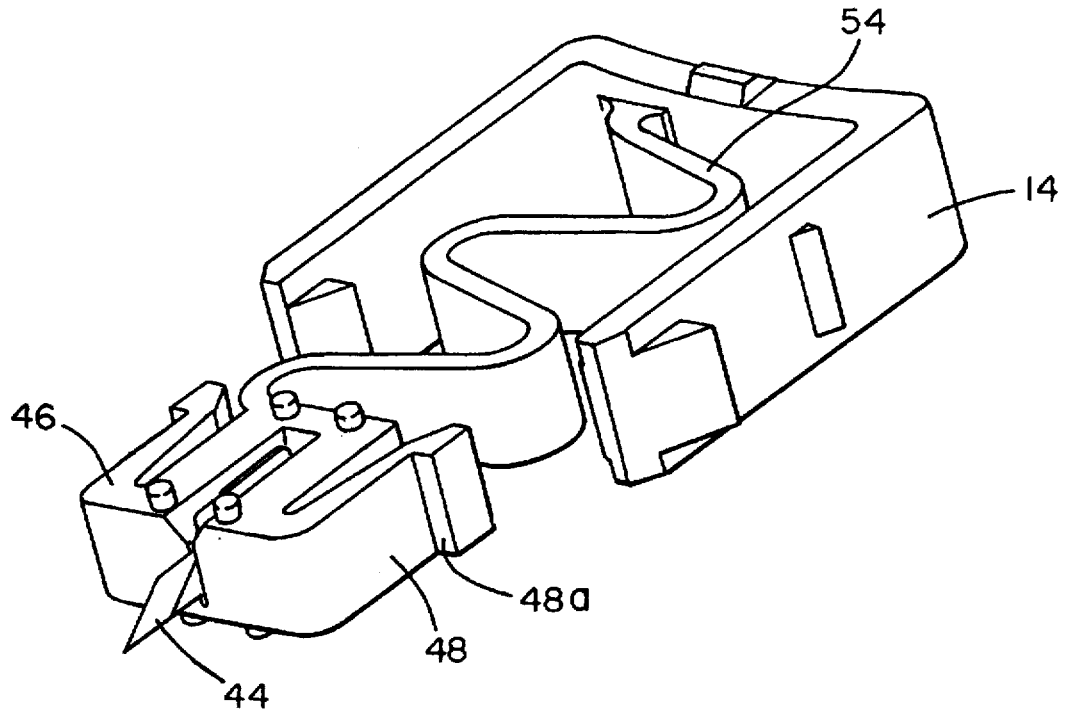
FIG. 7 schematically shows a perspective view of the lancet structure 14 of FIG. 6 after the blade 44 has been inserted.

Metal molds for the holder (to mold one piece), metal molds for the lancet structure (to mold one piece excluding the covered pricking member) and metal molds for the covered pricking member (to mold eight pieces) were fabricated, and all the members molded by the metal molds were substantially the same as the holder and lancet structure shown in FIGS. 5 and 10, respectively.

The lancet structure was so arranged that the covered pricking member was press fit to the lancet structure.

As to the materials used, an ABS resin (Toyorac #500, commercially available from Toray Industries, Inc.) was selected for the holder, a polyacetal resin (of a copolymer type) (Tenac #4520, commercially available from Asahi Chemical Industry Co., Ltd.) was selected for the lancet structure and a linear low density polyethylene resin (#AJ 5380, commercially available from Mitsui-Nisseki Polymer Co., Ltd.) was selected for the covered pricking member.

For the blade, stainless steel 440 A (commercially available from Hitachi Metals, Ltd., 0.16 mm thickness) was selected. A transferring mold and a stamping out mold (for one piece) were fabricated and blades each having a predetermined shape (not separated and connected to a carrier) were produced using a pressing machine (ten-ton type). An edge portion of the blade was then ground and abraded by means of a blade grinder.

The metal molds were installed on to a horizontal injection molder (forty-ton type, commercially available from Nissei Plastic Industrial Co., Ltd.), and the holders were produced using the ABS resin. The metal molds for the lancet structure were similarly installed, and the lancet structures were produced using the acetal resin.

Then, the metal molds for the resin covered pricking member were installed onto a vertical injection molder (thirty-ton type, commercially available from Nissei Plastic Industrial Co., Ltd.), and the blades (eight pieces) connected to the carrier were inserted into the molds, so that the resin covered pricking members were obtained using the PE resin. After the molding, notches having a depth of 0.3 to 0.35 mm were provided onto both sides of portions beside a convex engaging portion of the resin covered pricking member with a tool containing a razor blade (the notch did not reach the pricking member). Then, the resin covered pricking members were separated from the carrier to have individual pieces.

One hundred of the holders 16, the lancet structures 14 and the resin covered pricking members 84 each were thus produced.

The above molding processes were conventional and no specific technique was required.

Firstly, the resin covered pricking member 84 was connected to the lancet body 46 by means of press fitting using a bench pressing machine. The lancet connected structure was then inserted into the holder 16 through the opening 20 by inserting such that a tip portion 98 of the resin covered pricking member 84 was in the holder 16 first. The insertion itself was smoothly carried out since a cut away portion was formed at the tip of the resin covered pricking member for easy reception (for example, as shown in FIG. 12) and guiding channels 80 were formed inside the holder (thus, the spring structure is automatically controlled to have a predetermined orientation and attitude).

In the examples, as the lancet structure 14 integrally connected to the covered pricking member 84 proceeded ahead inside the holder, the first stops 92 of the resin covered pricking member 84 contacted the end wall 96 of the holder having the aperture 26. Although the width of the first stops is larger than that of the aperture, the first stops easily passed through the aperture 26 since the resin of the stops was the PE and the tapers for the easy reception were provided to the stops. Then, the lancet structure abutted against the stops 34 provided along the side surfaces of the holder, and stopped proceeding. In this position, the second stops 94 were not exposed from the end surface 96 of the holder, but were held in the predetermined position in the holder (as shown in FIG. 13).

In such a position, the inventor tried to force the resin covered pricking member 84 into the holder 16, and confirmed that it was impossible to do so since the first stops 92 had the irreversible shape which does not allow retraction into the holder 16. Thus, the first stops 92 function as explained above.

Next, in order to have the lancet to be ready to use, the holder 16 was held by the left hand and tip portion 96 of the resin covered pricking member was pinched using two fingers of the right hand, and then the tip portion 96 was pulled. The entire resin cover 82 was pulled out of the holder 16 with the second stops 94 passing freely through the aperture 26 (FIG. 14 schematically shows this position). The resin cover 82 was broken at the notch as predetermined and the pricking member 44 was exposed. (The lancet body of the lancet structure 14 did not move when the resin cover was removed since it was held by engagement of the stops 34 with the arms 48 as shown in FIG. 14).

Thereafter, when the lancet structure 14 was further depressed into the holder 16, the engagement condition was released so that the lancet structure 14 (including the blade) was ejected. This ejection process was recorded using an ultra-high speed VCR (video tape recorder) and then the ejection was checked by playing back the video tape. Thus, it has been confirmed that the blade was properly exposed through the aperture 26 to the outside and then properly returned into the inside of the holder.

The samples used in the above examples had the following sizes:

Notch depth (each of the both sides): 0.3 to 0.35 mm

Holder aperture (26): 4.7 mm×3.1 mm

Holder inside height: 4.3 mm

Width of first stops: 4.9 mm

Width of second stops: 5.4 mm

Then, the inventor tried to twist the resin cover 82 without drawing. However, it could not be twisted since the second stops 94 had a larger width than that of the inside height of the holder.

What is claimed is:

1. A lancet assembly comprising a holder and a lancet structure, the lancet structure being at least partially disposed within the holder, the lancet structure comprising a lancet member having a pricking member and a molded resin shield encasing the pricking member to prevent exposure and maintain sterility, and an ejector for ejecting the lancet member, the holder comprising an aperture through which the pricking member may be ejected during use, and the molded resin shield comprising two pairs of stops on its outside surface, one pair of stops being substantially adjacent the aperture, and the other pair of stops being positioned subjacent the aperture prior to use of the lancet assembly.

2. The lancet assembly according to claim 1, wherein the lancet structure further comprises a lancet body, the lancet body and the lancet member having portions which mate with each other so that the lancet body and the lancet member are tightly engaged, the holder comprises an aperture through which the pricking member may be ejected during use, and the molded resin shield comprises two pairs of stops on its outside surface, one pair of stops being substantially adjacent the aperture, and the other pair of stops being positioned subjacent the aperture prior to use of the lancet assembly.

3. The lancet assembly according to claim 1, wherein the molded resin shield comprises at least one notch at a predetermined position at which the resin shield is to be broken whereby the resin shield may be easily broken to expose the pricking member when pulled along an ejection direction of the pricking member, the holder comprises an aperture through which the pricking member may be ejected during use, and the molded resin shield comprises two pairs of stops on its outside surface, one pair of stops being substantially adjacent the aperture, and the other pair of stops being positioned subjacent the aperture prior to use of the lancet assembly.

4. The lancet assembly according to claim 2, wherein the molded resin shield comprises at least one notch at a predetermined position at which the resin shield is to be broken whereby the resin shield may be easily broken to expose the pricking member when pulled along an ejection direction of the pricking member, the holder comprises an aperture through which the pricking member may be ejected during use, and the molded resin shield comprises two pairs of stops on its outside surface, one pair of stops being substantially adjacent the aperture, and the other pair of stops being positioned subjacent the aperture prior to use of the lancet assembly.

5. The lancet assembly according to claim 1, wherein the pricking member is in the form of a blade.

6. The lancet assembly according to claim 2, wherein the pricking member is in the form of a blade.

7. The lancet assembly according to claim 3, wherein the pricking member is in the form of a blade.

8. The lancet assembly according to claim 4, wherein the pricking member is in the form of a blade.

9. The lancet assembly according to claim 1, wherein the pricking member is in the form of a needle.

10. The lancet assembly according to claim 2, wherein the pricking member is in the form of a needle.

11. The lancet assembly according to claim 3, wherein the pricking member is in the form of a needle.

12. The lancet assembly according to claim 4, wherein the pricking member is in the form of a needle.

* * * * *

UNITED STATES PATENT AND TRADEMARK OFFICE
CERTIFICATE OF CORRECTION

PATENT NO.  :  5,628,765
DATED       :  May 13, 1997
INVENTOR(S) :  Susumu Morita It is certified that error appears in the above-identified patent and that said Letters Patent is hereby corrected as shown below:

In Claim 1, column 14, line 36: "sterility, and" should read "sterility and".

Signed and Sealed this

Twelfth Day of August, 1997

*Attest:*

BRUCE LEHMAN

*Attesting Officer*      *Commissioner of Patents and Trademarks*